United States Patent
Scott et al.

(10) Patent No.: US 7,150,184 B1
(45) Date of Patent: Dec. 19, 2006

(54) DENSITY INDEPENDENT MOISTURE ANALYZER

(75) Inventors: Bentley N. Scott, Garland, TX (US); Enrique Osvaldo Capone, Garland, TX (US)

(73) Assignee: Phase Dynamics, Inc, Richardson, TX (US)

( * ) Notice: Subject to any disclaimer, the term of this patent is extended or adjusted under 35 U.S.C. 154(b) by 69 days.

(21) Appl. No.: 10/928,621

(22) Filed: Aug. 27, 2004

Related U.S. Application Data

(60) Provisional application No. 60/498,180, filed on Aug. 27, 2003.

(51) Int. Cl.
*G01N 25/56* (2006.01)

(52) U.S. Cl. ............... 73/73; 324/640; 324/643

(58) Field of Classification Search ............. 73/73; 324/640, 643
See application file for complete search history.

(56) References Cited

U.S. PATENT DOCUMENTS

| | | | | |
|---|---|---|---|---|
| 3,186,225 A | * | 6/1965 | Freeman, Jr. et al. | .... 73/335.05 |
| 4,606,222 A | * | 8/1986 | Stockmeyer | ............... 205/788 |
| 5,046,356 A | * | 9/1991 | Osaki et al. | ................ 73/73 |
| 5,767,685 A | * | 6/1998 | Walker | .............. 324/640 |
| 6,025,724 A | * | 2/2000 | Moshe et al. | ............. 324/640 |
| 6,161,422 A | * | 12/2000 | Thomas et al. | .............. 73/38 |
| 6,480,141 B1 | * | 11/2002 | Toth et al. | ................ 342/22 |
| 2002/0005725 A1 | * | 1/2002 | Scott | ................ 324/637 |

FOREIGN PATENT DOCUMENTS

SU  1635101 A  *  5/1988

OTHER PUBLICATIONS

"The New MicroMoisture Instrument", http://web.archive.org/web/20010518062016/http://www.moisturedetection.com/, archived on May 18, 2001.*

* cited by examiner

*Primary Examiner*—Michael Cygan
(74) *Attorney, Agent, or Firm*—Groover & Holmes

(57) ABSTRACT

Systems and methods for the on-site determination of water content in crude oil. The water content of crude oil is determined by mixing a sample of the crude oil with a fixed amount of molecular sieves. The electromagnetic characteristics of the molecular sieves upon mixing with the sample are then measured and used to determine the water content of the sample. This provides a simple approach to measuring the moisture content in crude oil that is extremely fast, accurate, and reproducible without the use of hazardous chemicals.

48 Claims, 11 Drawing Sheets

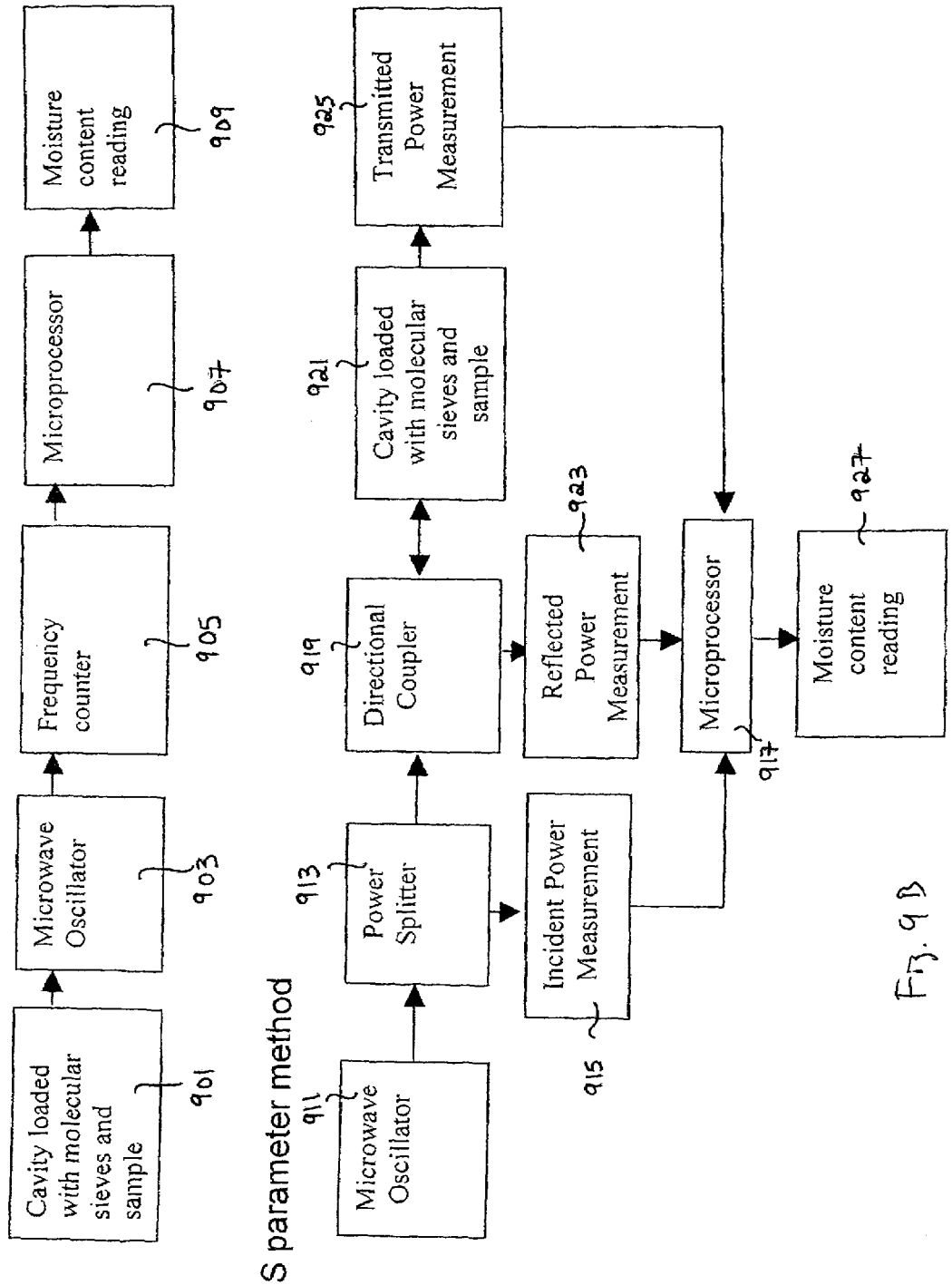

DENSITY INDEPENDENT MOISTURE ANALYZER

CROSS-REFERENCE TO RELATED APPLICATIONS

This application claims priority from U.S. Provisional Application 60/498,180, filed 27 Aug. 2003, which is hereby incorporated by reference.

FIELD OF THE INVENTION

The present inventions relate generally to a laboratory or portable measurement method and system, and more particularly, to a method and system for the point of sale measurement of the water content in a petroleum sample.

BACKGROUND AND SUMMARY OF THE INVENTION

Background: Conventional Methods for Measuring Water Content

A determination of water content in crude oil is required to measure accurately net volumes of actual oil in sales, taxation, exchanges, and custody transfers. The water content of crude oil is also significant because it can cause corrosion of equipment and problems in processing. Thus, various methods have been developed for measuring the water content of crude oil.

Background: Karl Fischer Titration Method

In 1935, the German scientist, Karl Fischer, developed a titrimetric determination of water content using a reagent that contained iodine, sulphur dioxide, anhydrous pyridine and anhydrous methanol. This method can be subdivided into two main techniques: volumetric titration and coulometric titration.

The volumetric technique involves dissolving the sample in a suitable solvent and adding measured quantities of a reagent containing iodine until an end point is reached. This end point is determined potentiometrically using a platinum electrode. When all of the water has reacted, the platinum measuring indicator electrode will electronically instruct the burette to stop dispensing. The volume of KF reagent dispensed is recorded. Based on the concentration of iodine in the KF reagent, the amount of water present is then calculated.

However, even with automatic or semi-automatic instruments commercially available, there are certain problems associated with this technique. These problems include long analysis time, required reagent calibration, and high reagent consumption rate.

In the coulometric technique developed by Meyer and Boyd in 1959, the sample is introduced into a mixture of pyridine/methanol that contains iodide ions and sulphur dioxide. The electrode system consists of an anode and cathode platinum electrodes that conduct electricity through the cell. Iodine is generated at the anode and reacts with any water present. The production of iodine is directly proportional to the amount of electricity according to Faraday's Law as shown in the equation:

$$2I^- - 2e \rightarrow I_2.$$

According to the stoichiometry of the reaction, 1 mole of iodine will react with 1 mole of water, and combining this with coulometry, 1 milligram of water is equivalent to 10.71 coulombs of electricity. Therefore, it is possible to directly determine the amount of water present in a sample by measuring the electrolysis current in couloumbs. The platinum indicating electrode voltametrically senses the presence of water and continues to generate iodine until all the water in the sample has been reacted.

From this titration, the on board microprocessor calculates the total amount of current consumed in completing the titration and the time to completion in seconds. Based on the relationship between coulombs and iodine, the exact amount of iodine generated is recorded. Since water reacts in the 1:1 ratio with iodine, the amount of water can be calculated.

Although the original Karl Fischer reagent contained pyridine, most reagent manufacturers now use other amines such as imidazol.

Karl Fischer titration is one of the most widely used techniques for measuring the water content in a large range of samples. However, it has limits that affect its usefulness for on-site detection of moisture in petroleum samples. For example, it utilizes hazardous reagents that require the user to exercise care in the storing, handling, and disposing of the reagents. The small sample size utilized by the techniques causes errors. Also, the technique cannot measure water percentages over 1% accurately.

(Please see *Manual of Petroleum Measurement Standards*, Chapter 10.7—*Standard Test Method for Water in Crude Oils by Potentiometric Karl Fischer Titration* and Chapter 10.9—*Determination of Water in Crude Oils Coulometric Karl Fischer Titration* for the complete protocols which are hereby incorporated by reference.)

Background: Centrifuge Method

In the standard method for determining the water content in crude oil by centrifuge, equal volumes of a crude oil sample and water saturated toluene are placed into two cone-shaped centrifuge tubes. The tubes are then corked and placed into a centrifuge. The tubes are then spun for 10 minutes at a minimum relative centrifugal force of 600 calculated from the following equation:

where:
  rcf=relative centrifugal force and
  d=diameter of swing measured between tips of opposite tubes when in rotating position, mm.

Immediately after the centrifuge comes to rest following the spin, the combined volume of water and sediment at the bottom of each tube is read and recorded. The spin is then repeated until the combined volume of water and sediment remains constant for two consecutive spins. The final volume of water is then recorded for each tube.

The standard method for determining the water content in crude oil by centrifuge is not entirely satisfactory. The amount of water detected is almost always lower than the actual water content. Therefore, when a high accurate value is required, another method must be used. This method also requires hazardous solvents, and has very poor accuracy and reproducibility.

(Please see *Manual of Petroleum Measurement Standards*, Chapter 10.3—*Standard Test Method for Water and Sediment in Crude Oil by the Centrifuge Method (Laboratory Procedure)* for the complete protocol which is hereby incorporated by reference.)

Background: Distillation Method

In the standard test for determining the water content in crude oil by distillation, the crude oil sample is heated under reflux conditions with a water immiscible solvent that co-distills with the water in the sample. The condensed solvent and water are continuously separated in a trap wherein the water settles in the graduated section of the trap, and the solvent returns to the distillation flask. The amount of water can then be determined on a volume or a mass basis.

The precision of this method can be affected by water droplets adhering to surfaces in the apparatus and, therefore, not settling into the water trap to be measured. To minimize this problem, all apparatus must be chemically cleaned at least daily to remove surface films and debris that hinder the free drainage of water in the apparatus.

The drawbacks to this method include, for example, the fact that it utilizes hazardous solvents and produces hazardous vapors. This method also takes 2 to 3 hours to complete, and as with most distillation techniques, the accuracy and precision of the results will depend upon the skill of the technician performing the distillation.

(Please see *Manual of Petroleum Measurement Standards*, Chapter 10.2—*Standard Test Method for Water in Crude Oil Distillation* for the complete protocol which is hereby incorporated by reference.)

Background: Zeolite Molecular Sieves

Molecular sieves, as used in this specification, include any material that can effectively be used to sequester or restrain or retain molecules in a material, such as, but not limited to, water molecules in a non-aqueous liquid, whether by physical capture within a crystalline structure, absorptive properties, adsorption, hydrogen bonding, or other means.

One class of molecular sieves includes crystalline, hydrated metal aluminosilicates. The commercially important types of molecular sieves are synthetically made, but their structure is similar enough to naturally occurring minerals to be classified as zeolites. Although the crystal structures of some of the molecular sieves are quite different, their absorbent property derives from their crystalline structure.

The crystalline metal aluminosilicate molecular sieves have a simple polyhedra arrangement. Each polyhedron is a three-dimensional array of (Si, $AlO_4$) tetrahedral. The tetrahedra are formed by four oxygen atoms surrounding a silicon or aluminum atom. Each oxygen atom has two negative charges and each silicon atom has four positive charges. This structure permits a net sharing arrangement, building a tetrahedron uniformly in four directions. The trivalency of aluminum causes the alumina tetrahedron to be negatively charged, requiring an additional cation to balance the system. Thus, the final structure has sodium, potassium, or calcium cations in the network. These "charge balancing" cations are the exchangeable ions of the zeolite structure.

Zeolites, one class of molecular sieves, exhibit electrical conductivity of an ionic type due to the migration of cations through the channel structure. The ability of the cations to carry a current depends upon their ionic mobility, charge, size, and location in the structure. The addition of water molecules to a dehydrated zeolite structure produces a pronounced change in the electrical conductivity of the zeolite. The conductivity of the zeolite increases with the amount of water present. The activation energy for conduction decreases with increasing adsorption of water. The influence of water is different for different zeolites. In some cases, the activation energy for conduction in a zeolite containing divalent ions is approximately twice that of a zeolite containing univalent ions.

When formed, this crystalline network is full of water, but with moderate heating, the moisture can be driven from the cavities without changing the crystalline structure—leaving countless cavities with their tremendous combined surface area and pore volume available for adsorption of water or other materials.

With their large surface area and pore volume, molecular sieves then can perform virtually all the adsorption duties presently carried out by other absorbents. In addition, molecular sieves allow for a new dimension in process control because the pores of the crystalline network are uniform rather varied. Therefore, molecular sieves are able to differentiate molecules on the basis of molecular size and configuration.

Hence, molecular sieves utilize two adsorption mechanisms. They exhibit the capillary condensation phenomenon as a result of their large surface area and pore volume, and their polar surfaces have an electrostatic attraction for polar molecules such as water. This allows molecular sieves to be stronger absorbents than silica gel or alumina.

Another advantage to molecular sieves is that they can be packaged in foil-sealed bags to prevent moisture adsorption. This allows them to have long term stability and makes them easy to use. Also, the measured quantity of molecular sieves can be accurately controlled.

Although this application refers to the adsorptive properties and activities of molecular sieves, it understood that a certain amount of absorption also takes place. Therefore, for the sake of simplicity, references to the adsorptive properties and activities of molecular sieves are intended to include any absorptive properties and activities as well.

Background: The "Load-Pulled" Effect

It is well known to electrical engineers generally (and particularly to microwave engineers) that the frequency of an RF (radio frequency) oscillator can be "pulled" (i.e. shifted from the frequency of oscillation which would be seen if the oscillator were coupled to an ideal impedance-matched pure resistance), if the oscillator sees an impedance which is different from the ideal matched impedance. Thus, a varying load impedance may cause the oscillator frequency to shift.

The present application sets forth various innovative methods and systems which take advantage of this effect. In one class of embodiments, an unbuffered RF oscillator is loaded by an electromagnetic propagation structure which is electromagnetically coupled, by proximity, to a material for which real time monitoring is desired. The net complex impedance seen by the oscillator will vary as the characteristics of the material in the electromagnetic propagation structure vary. As this complex impedance changes, the oscillator frequency will vary. Thus, the frequency variation (which can easily be measured) can reflect changes in density (due to bonding changes, addition of additional molecular chains, etc.), ionic content, dielectric constant, or microwave loss characteristics of the medium under study. These changes will "pull" the resonant frequency of the oscillator system. Changes in the medium's magnetic permeability will also tend to cause a frequency change, since the propagation of the RF energy is an electromagnetic process which is coupled to both electric fields and magnetic fields within the transmission line.

Background: Aluminum Oxide for Moisture Adsorption

The use of aluminum oxide for moisture adsorption is well known in the industry. The surface attracts and retains water molecules by association with the bonds. Since this is a weak attraction there is a point at which the absorption and desorption reaches an equilibrium with the surrounding moisture content. Moisture measurements have been made with capacitance measurements using a very thin aluminum oxide surface with imbedded electrodes. When the water is absorbed the capacitance changes and therefore a measurement is made. This surface must be thin in order to allow the water molecules to accumulate in a region where the electrical field is present.

For further background and information on load pulled systems, the reader is referred to U.S. Pat. No. 6,630,883 to Scott, which is hereby incorporated by reference.

Density Independent Moisture Analyzer

The present application describes systems and methods for the on-site determination of water content in crude oil.

The present innovations include, in one embodiment, placing a material to be tested in a container or package of a molecular sieve material. This container is then placed in a microwave measurement system (or other scattering parameter measuring system). By measuring the effects of the sample on scattering parameters, the sample can be characterized.

For example, the innovations can detect an amount of water in another material, such as crude oil, by placing a crude oil sample in the container with the molecular sieves, and by measuring the effects on the scattering parameters, an estimate of the water content of the oil can be determined.

Hence, the disclosed innovations provide a simple approach to measuring the moisture content in crude oil that is extremely fast, accurate, and reproducible without the use of hazardous chemicals.

BRIEF DESCRIPTION OF THE DRAWINGS

The disclosed inventions will be described with reference to the accompanying drawings, which show important sample embodiments of the invention and which are incorporated in the specification hereof by reference, wherein:

FIGS. 9A and 9B shows general block diagrams of the load-pulled method and the phase/amplitude measuring microwave method utilized by the present inventions.

DETAILED DESCRIPTION OF THE PREFERRED EMBODIMENTS

The numerous innovative teachings of the present application will be described with particular reference to the presently preferred embodiment (by way of example, and not of limitation).

In one embodiment, the present innovations involve obtaining a sample of petroleum for moisture determination, and placing the contents of a foil-sealed package of molecular sieves and the sample into a microwave cavity, coaxial line, or similar transmission line system. The molecular sieve will occupy the majority of the volume of the cavity or line. Hence, the bulk volume seen by the microwave energy effectively has a single density altered only slightly by adding the petroleum sample. The changing density of the petroleum sample, for example, 680 kg/m$^3$ to 980 kg/m$^3$, negligibly offsets the resultant moisture content.

The another embodiment, the cavity or transmission line is arranged such that the sample and sieve would be first placed in a plastic or paper container, or any material that would not be absorptive of microwave energy, and then placed inside the microwave measurement system.

The system would then be loaded with molecular sieves and the petroleum sample (molecular sieves having already removed the moisture from the sample). The container, molecular sieves, and the sample are configured such that the consistent weight percentage of molecular sieves and a fixed amount of sample are controlled accurately.

In one embodiment, the microwave system measures phase and amplitude via scattering parameters of the system. In another embodiment, the microwave system is a load-pulled microwave system.

Although both systems measure the parameters of the microwave propagation parameters, they determine the moisture content by different means. Specifically, a non-load pulled microwave system measures the amplitude phase of the waves, such as reflections, transmission losses, and phase angles. These measurements are used to determine the change in scattering parameters. This changes would then be compared to a previously generated calibration to then output by screen, digital, or analog the moisture content of the sample. By contrast, a load-pulled microwave system uses the changes in the frequency readings of the scattering parameters of the molecular sieves after being mixed with the sample to determine the moisture content of the sample.

Both methods take less than a few seconds to determine the moisture content.

Once the moisture of the sample was determined, the sample container would be removed leaving the microwave portion clean and free for the next analysis. The sample container would then be cleaned and reused or disposed of in a proper manner.

Figure 1A:
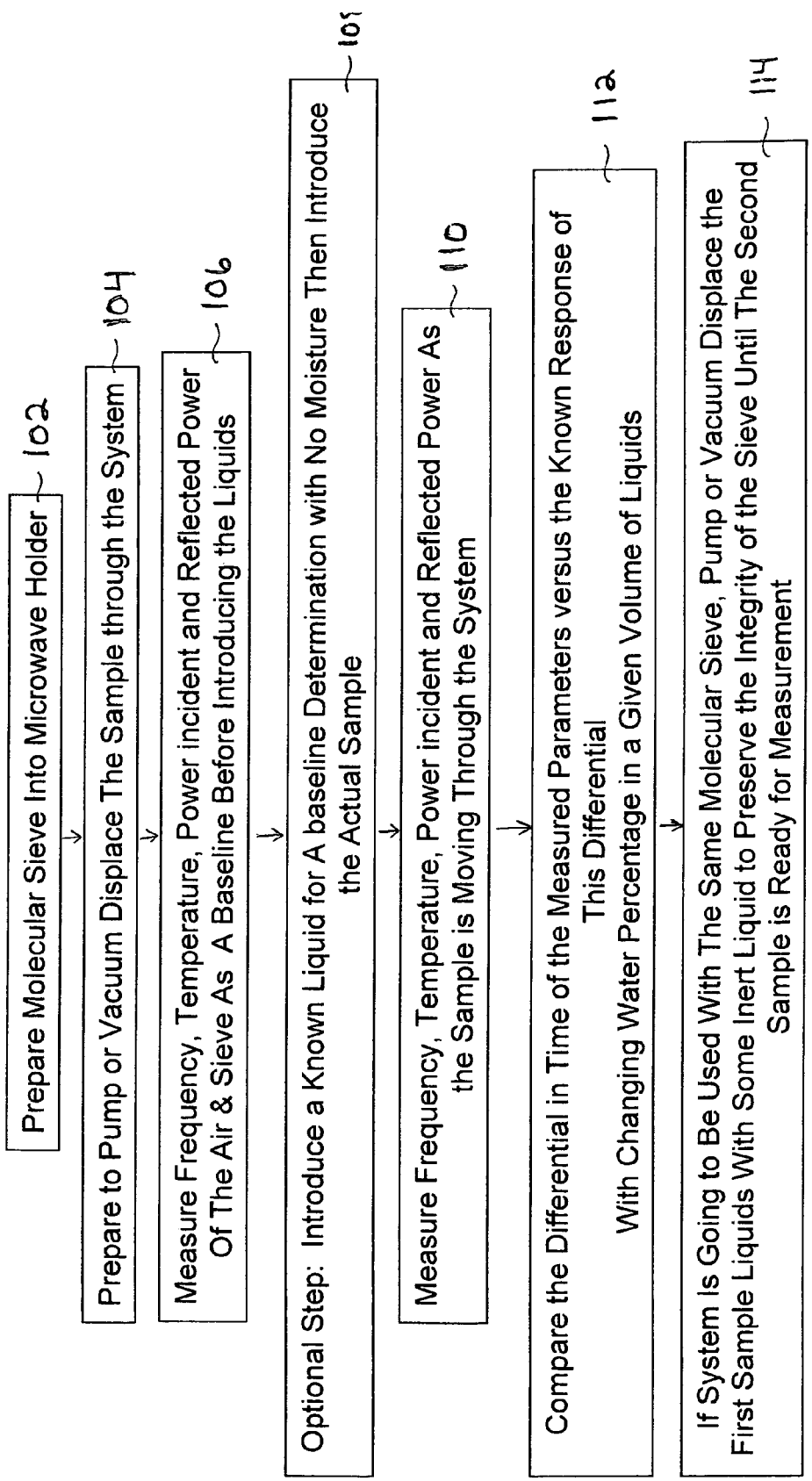
FIGS. 1A–1C are flow charts of preferred embodiments of the present inventions.

FIG. 1A is a flow chart of a preferred embodiment of the present inventions. In this embodiment, molecular sieves are placed into a microwave holder (step 102). A pump or vacuum is then prepared to displace the sample liquids through the system (step 104). Alternatively, the sample need not be passed though, for example when measuring a static sample. In on embodiment, the frequency, temperature, power incident, and reflected power of the molecular sieves are measured to generate a baseline before introducing the sample liquids (step 106). In another embodiment, an optional step would be to introduce a known liquid with no moisture to generate a baseline before introducing the sample liquids (step 108). The frequency, temperature, power incident, and reflected power of the air and molecular sieves are measured as a sample of liquids is moving through the system (step 110). The differential in time of the measured parameters is compared against the known response of this differential with changing water percentage in a given volume of liquids (step 112) to determine the moisture content of the sample. If the system is going to be used to measure a second sample of liquids with the same molecular sieves, a pump or vacuum is used to displace the first sample of liquids with an inert liquid to preserve the integrity of the molecular sieves until the second sample of liquids is ready for measurement (step 114).

Figure 1B:
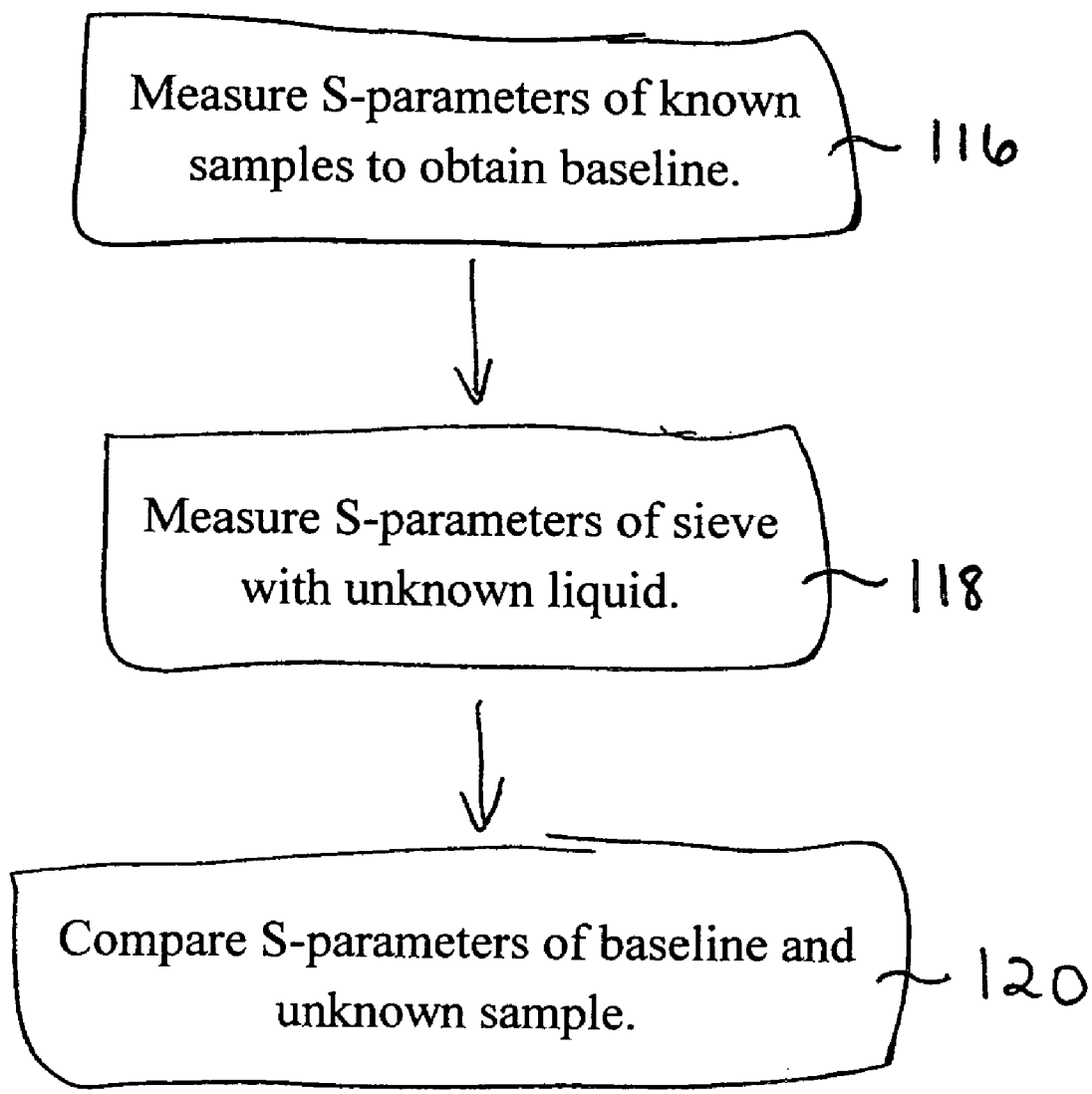

FIG. 1B shows a flowchart consistent with implementing a preferred embodiment of the present invention. This flowchart provides a broad overview of the present innovations. First, s-parameters of a known sample are measured using a microwave oscillator system to obtain baseline curves (step 116). In this step, materials with known water content, for example, in oil are measured, and their effects on s-parameters are determined. By generating several such curves, liquids with unknown quantities can be measured (step 118) and the results compared with the baseline graphs to estimate, for example, the water content of the fluid (step 120). It is noted that the content of water in oil is only one example of what can be tested.

Figure 1C:
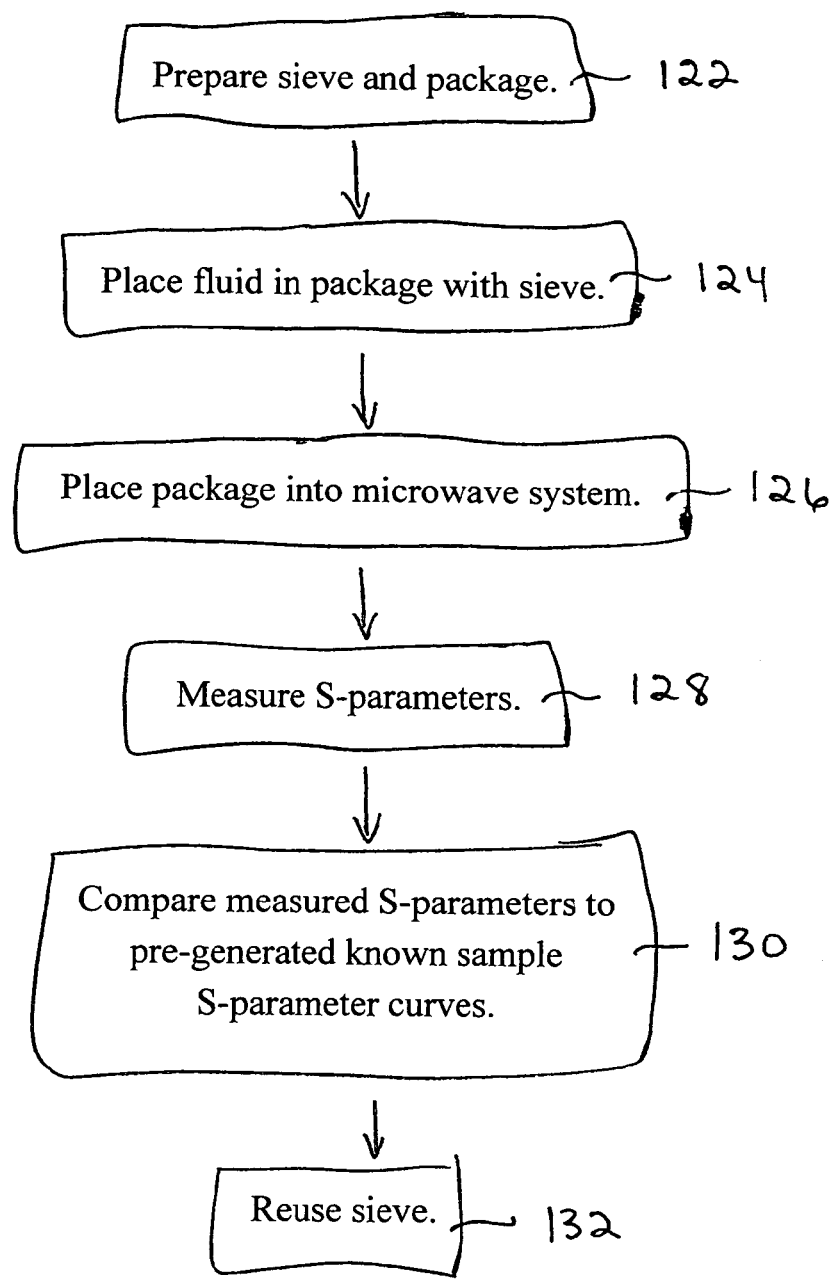

FIG. 1C shows a flowchart of process steps consistent with implementing a preferred embodiment of the present invention. First, the molecular sieve material is prepared and packaged (step 122). The fluid to be tested is placed in the package with the sieve material (step 124). Next, the package is placed in the microwave measurement system (step 126). The s-parameters of the sample are then measured (step 128) and compared to the pre-generated, known sample s-parameter curves (step 130) such as those discussed with respect to FIG. 1A. Finally, in some embodiments, the molecular sieve material is reused (step 132). This step can include some preparation of the sieve, such as a rinsing or resetting of some type, or it can simply be reused as-is.

The present invention can be practiced in more than one way. For example, two preferred embodiments use, respectively, the load pull method and the phase/amplitude measuring microwave oscillator coupling method, both of which measure scattering parameters (s-parameters) of the material to be tested. In the load pulling method, a non-buffered microwave oscillator is coupled to a network including the sample to be tested including a molecular sieve material. As the molecular sieve material absorbs, for example, water from, for example, crude oil, the permittivity of the sample and sieve combined will change. This change will cause a detectable change in the scattering parameters of the system. In the load pull method, the change is detected by measuring the shift in frequency of the microwave oscillator as it is influenced by the sample and sieve material. This frequency change is compared to a catalog of known frequency changes as caused by known samples and sieves.

In preferred embodiments, microwave frequencies are used to probe the system. The range of frequencies available for use with the present innovations is not intended to be limited to any particular range other than those which interact in a detectable way with the material being characterized. In preferred embodiments, a frequency range of 200–500 MHz is used, with the specific frequency depending on the cavity size (specifically, the two-dimensions seen end-on by the microwave oscillator) and the dielectric constant of the materials inside the probed container. Example dimensions include a 1"×3" container of any length.

In the phase and amplitude measurement scheme, a buffered microwave oscillator is coupled to a system including the molecular sieve material and the sample material to be tested. As the permittivity changes, so change the phase and amplitude of the incident, reflected, and transmitted waves through the system. These changes are detected by power detectors, which compare the results to known curves for known materials, such as, for example, crude oil having a known water content. In this way, for example, crude oil with an unknown water content can be characterized and its water content estimated by referring to the pre-generated curves. These and other embodiments are described more fully below.

Figure 2:
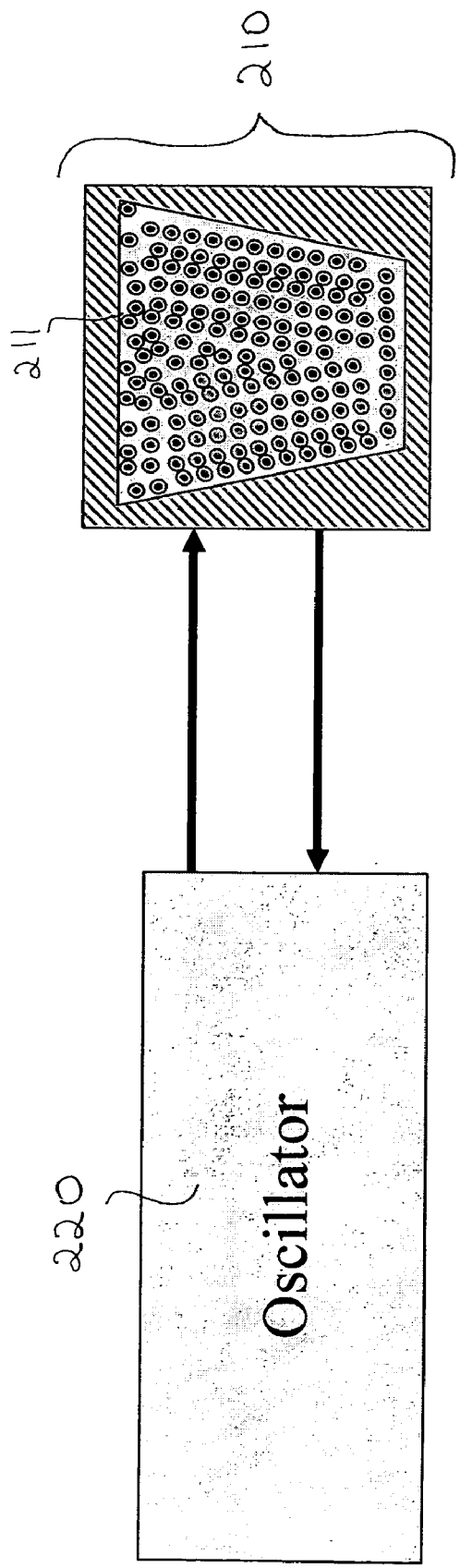
FIG. 2 shows the general layout of a preferred embodiment.

FIG. 2 shows the general layout of a preferred embodiment. This layout shows a measurement cavity 210 with a container 211 placed inside measurement cavity 210. Container 211 is shown filled with molecular sieves as well as a sample liquid to be measured. Measurement cavity 210 is coupled to a microwave measurement system 220 and preferably contains a known quantity of molecular sieves. Measurement system 220 can be a microwave measurement system that measures reflections, transmission losses, and phase angles. Measurement system 220 can also include a load-pulled oscillator system with a frequency counter. Cavity 210 can also be a transmission line or waveguide. Cavity 210 can be a microwave cavity waveguide or a transmission line arrangement.

Figure 3:
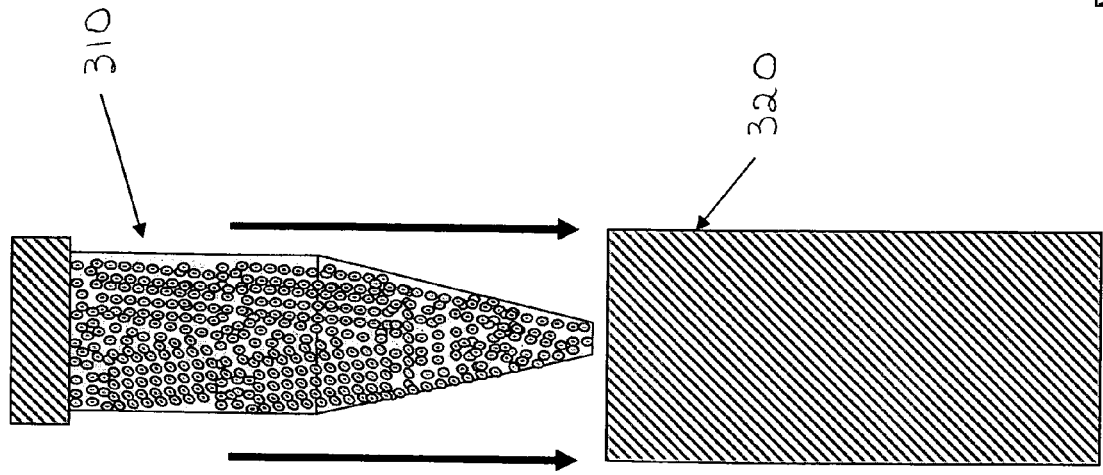
FIG. 3 shows a standard polymer centrifuge tube containing molecular sieves and a microwave measurement cavity designed to receive the tube.

FIG. 3 shows a standard polymer centrifuge tube 310 containing molecular sieve material and prepared with a liquid-tight lid. Cavity 320 designed to receive tube 310 is also shown. The cavity 320 of FIG. 3 is capable of being placed in the microwave measurement system of FIG. 2, as shown, for example, in FIG. 4.

Figure 4:
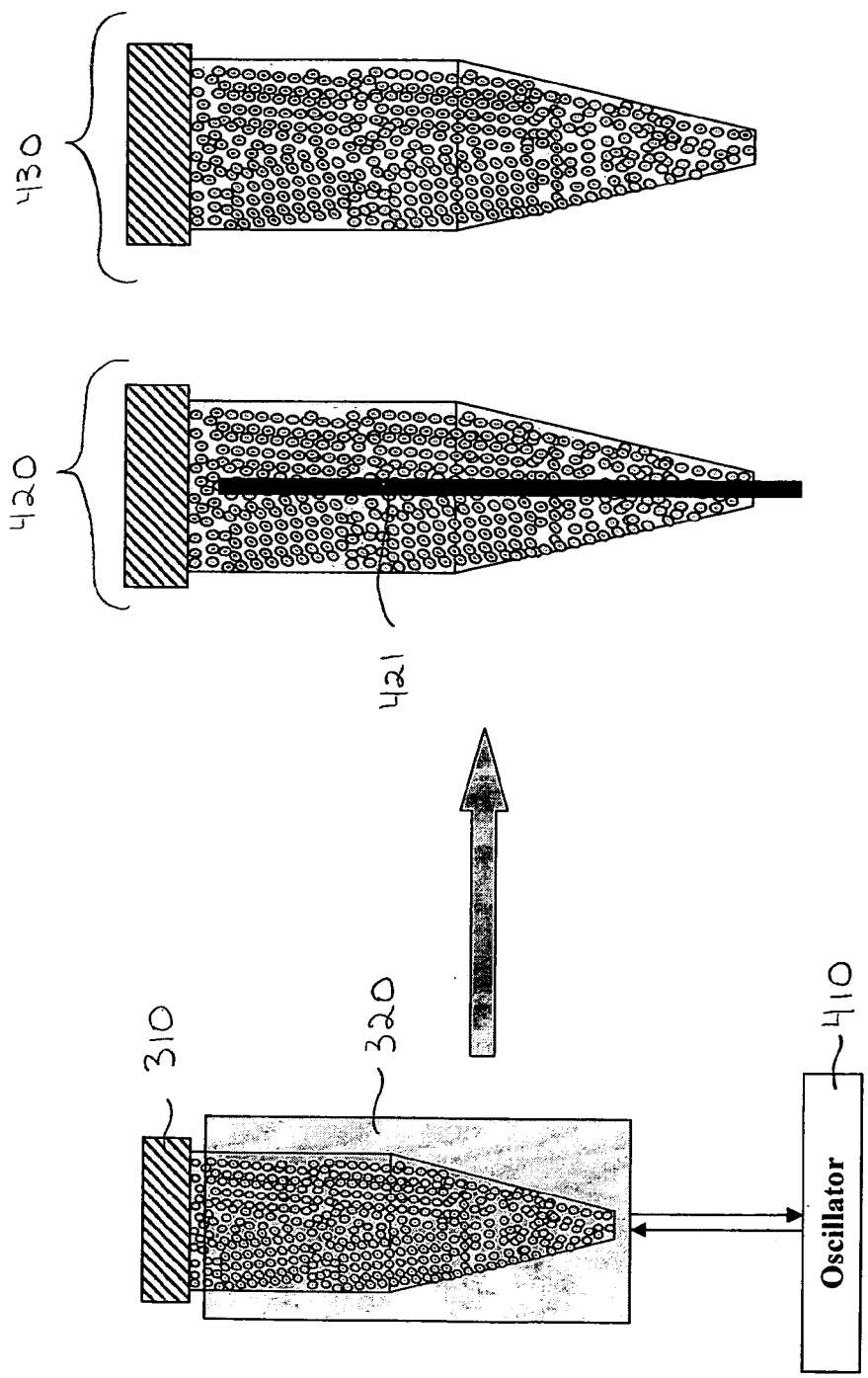
FIG. 4 shows the centrifuge tube inside the cavity which is coupled to an oscillator system.

FIG. 4 shows tube 310 inside cavity 320 and coupled to an oscillator 410. Tube 310 can be implemented with a center rod 421 for a coaxial system built into the tube as depicted by reference 420. Tube 310 can also be implemented without internal metal wave guiding for use in a cavity system as depicted by reference 430. Oscillator 410 includes oscillator circuitry and other circuitry, depending on the embodiment, such as shown in FIGS. 9A and 9B.

Figure 5:
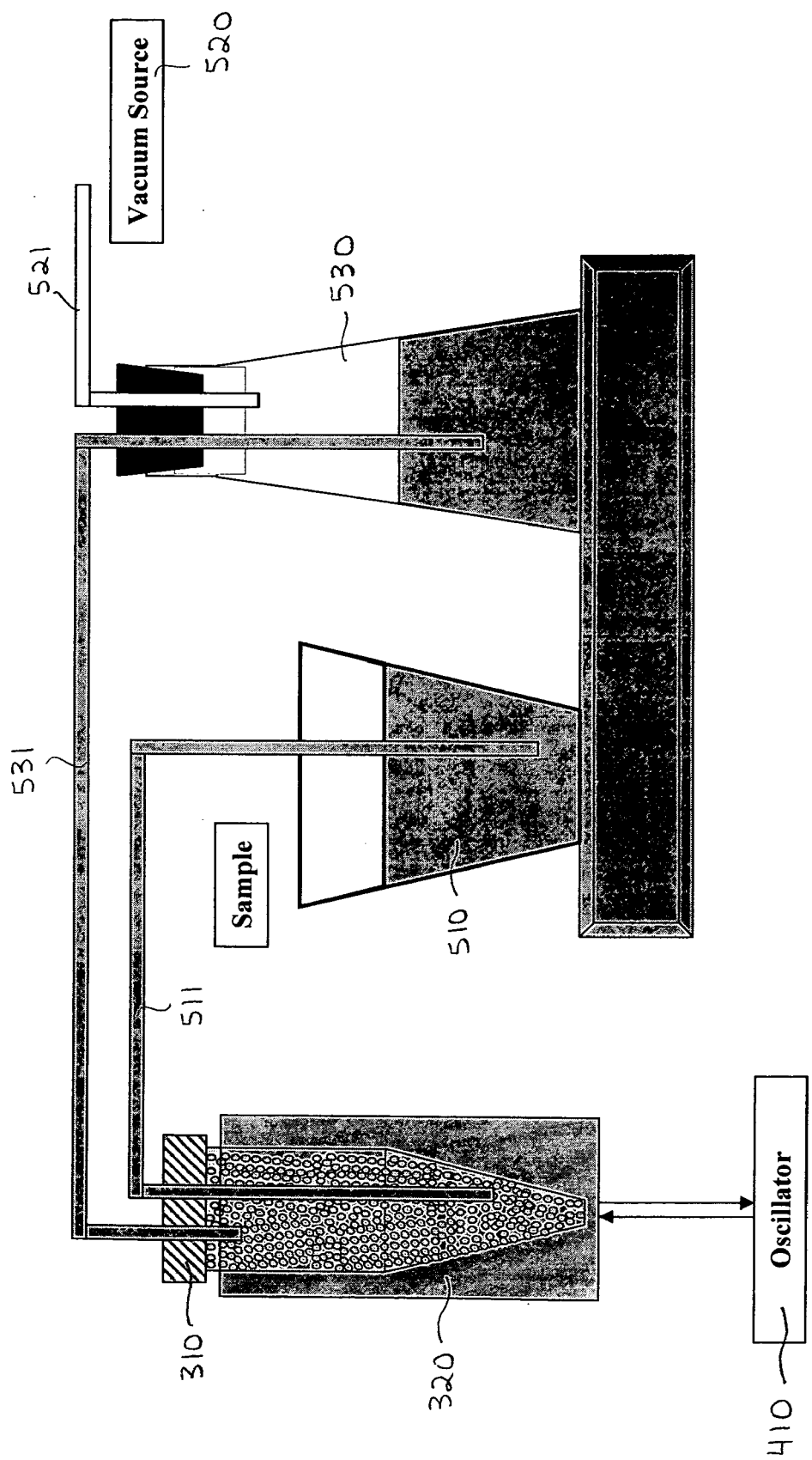
FIG. 5 shows a sample embodiment in which the sample is introduced into and displaced from the centrifuge tube by means of a vacuum source.

FIG. 5 shows tube 310 inside cavity 320 and coupled to oscillator 410. In this figure, sample 510 is introduced into tube 310 via port 511. Once sample 510 has been measured, a vacuum source 520 is used to purge sample 510 from tube 310 and into flask 530 via ports 521 and 531. This avoids contamination of the next sample, as well as minimizes disposal. Although this figure shows the sample purged into a flask, the sample may also be blown back into the main tank.

Figure 6:
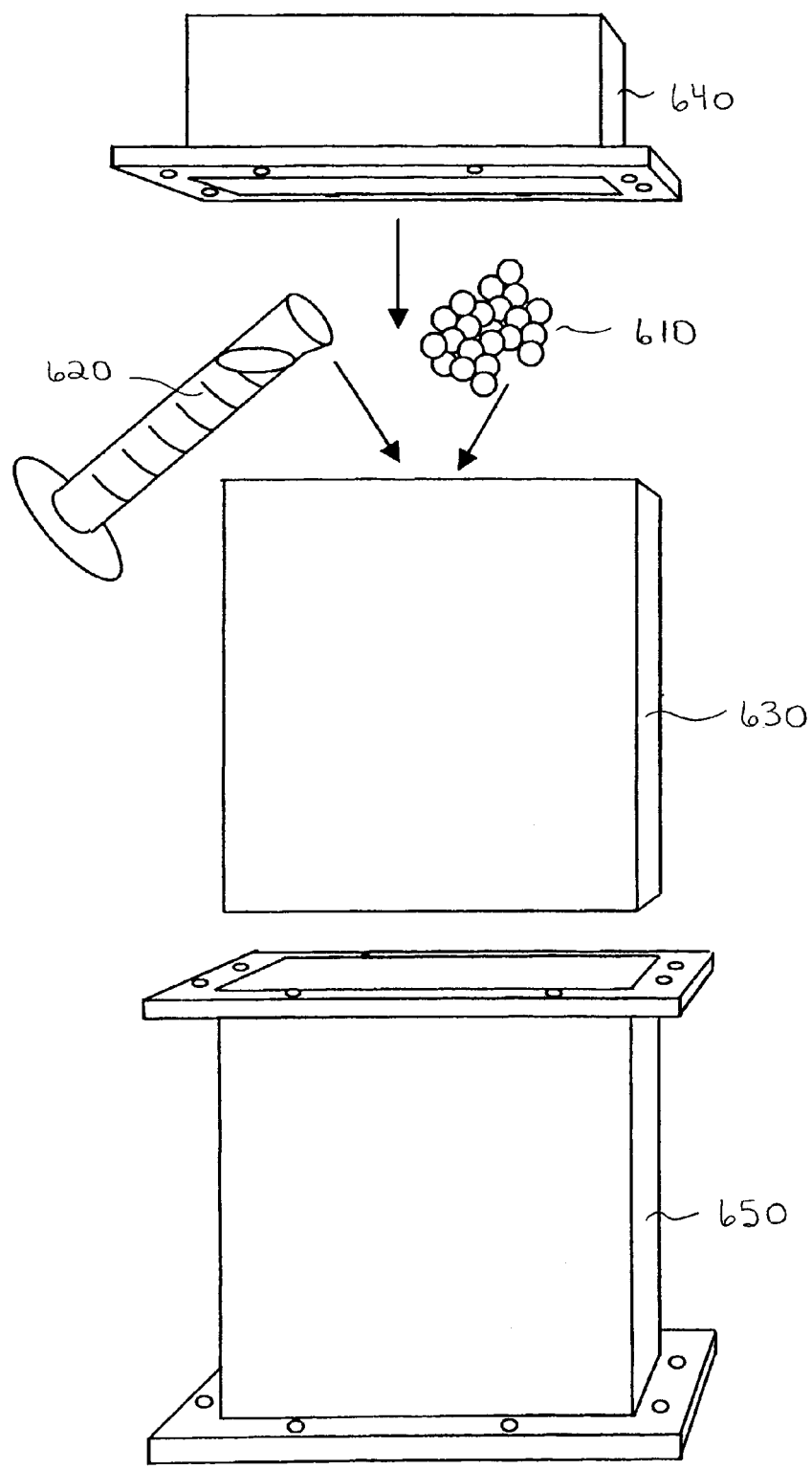
FIG. 6 shows another preferred embodiment of the present inventions utilizing a disposable container.

FIG. 6 shows another preferred embodiment of the present inventions utilizing a disposable container. In this embodiment, the molecular sieves 610 and sample 620 are placed into a preferably disposable container 630 and placed inside of the microwave measurement system comprising, in this example, a wave guide short circuit 640 and wave guide 650. Container 630 is preferably made of any material that would be consistent and not significantly absorptive of microwave energy, such as plastic, foam, or paper. In some embodiments, after the sample is tested, the sieve is recovered and reused.

Figure 7:
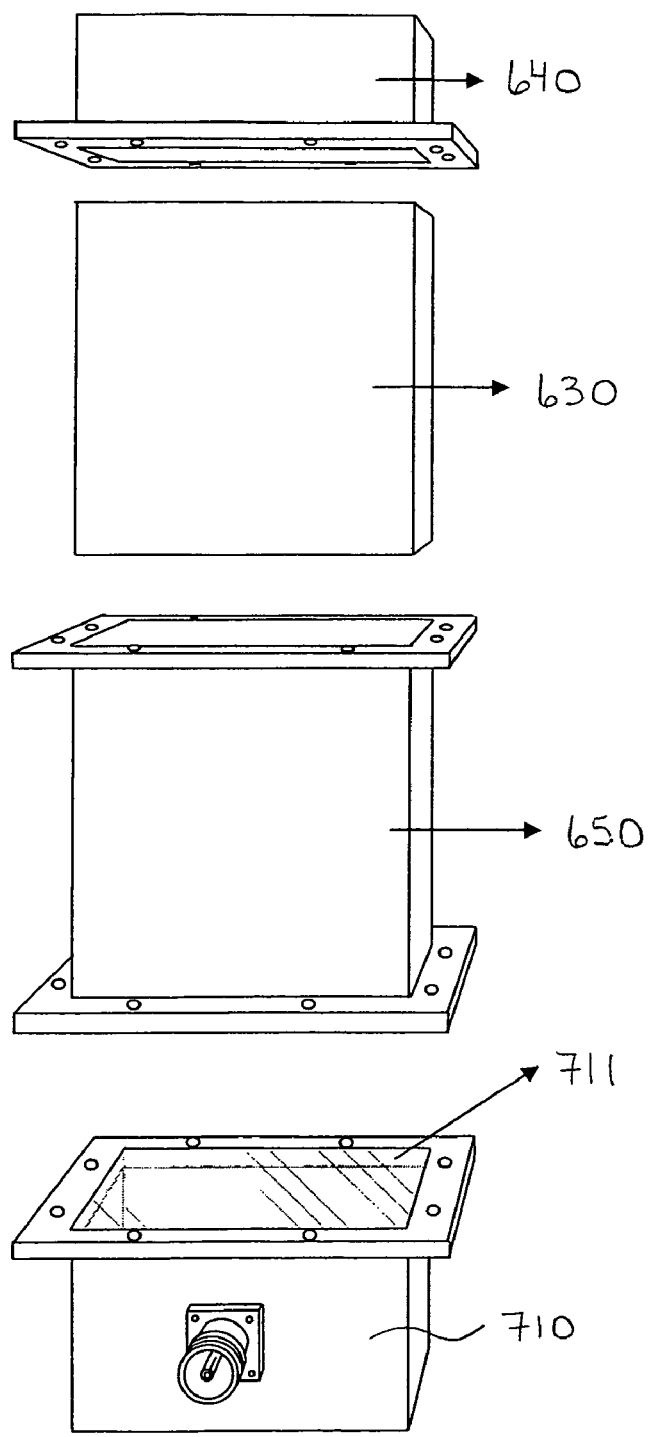
FIG. 7 shows the disposable container measured using the load-pulled method.

FIG. 7 shows an embodiment of container 630 measured using either the load-pulled method or the phase and amplitude measurement method. In this figure, disposable container 630, wave guide short circuit 640, and wave guide 650 are shown coupled to microwave input 710 with glass window 711. In this arrangement, as the microwaves are being passed though container 630, the frequency readings of the molecular sieves after being mixed with a sample liquid will be used by a microprocessor to determine the moisture content of the sample in container 630. In this example, the apparatus shows wave guide with microwave input 710, but no microwave output. This creates standing waves in the waveguide, with the walls acting as a cavity.

This example setup is consistent with either the load pulled or the phase-amplitude measuring systems.

Figure 8:
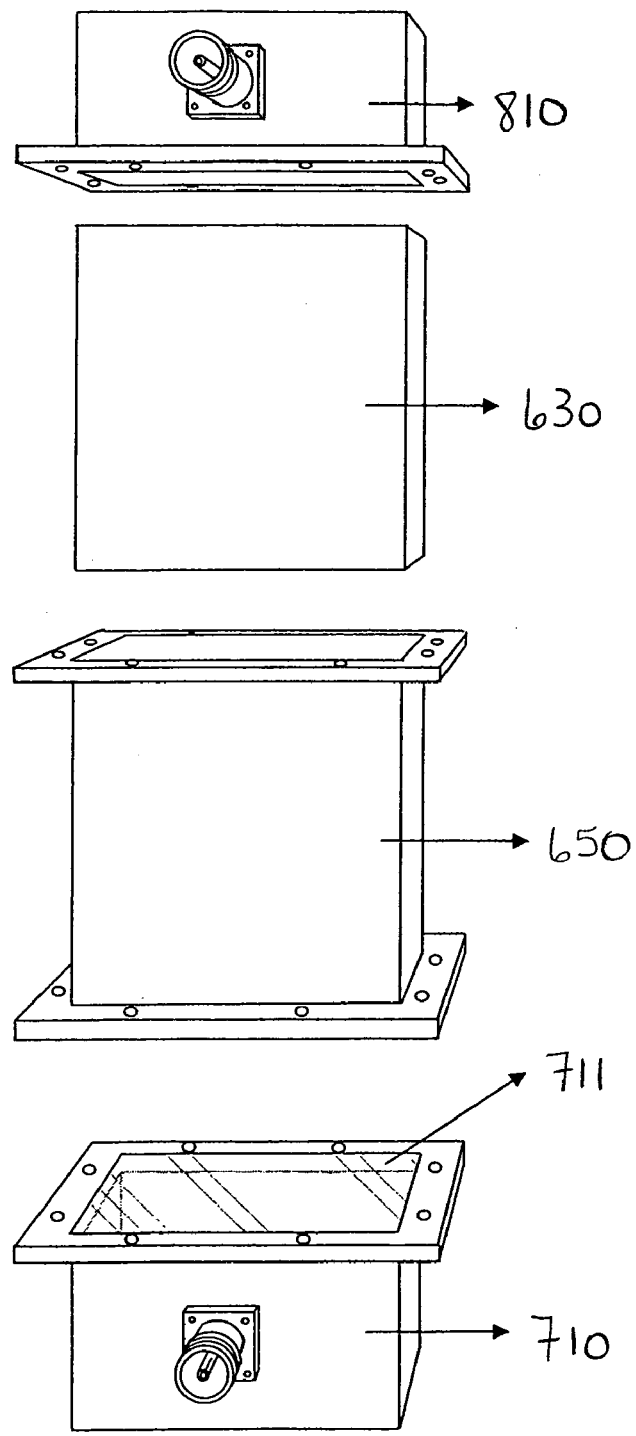
FIG. 8 shows the disposable container measured using a phase and amplitude measuring microwave method.

FIG. 8 shows disposable container 630 measured using a phase-amplitude measuring microwave method. In this figure, disposable container 630, wave guide 650, and microwave input 710 with glass window 711 are shown coupled to microwave output 810. In this arrangement, the microwave system would measure scattering parameters, such as reflections, transmission losses, and phase angles of the microwaves from output 810 that have passed though disposable container 630 after the molecular sieves have been mixed with a sample liquid. These parameters would then be compared to a previously generated calibration to determine the moisture content of the sample. Changes in these parameters are detected as changes in phase and amplitude of incident and reflected waves, for example, and are captured by power detectors, preferably situated at either end of the waveguide. Note also that this example shows the system as a transmission line system, with microwave input and output, one at either end.

FIG. 9A shows general block diagrams of the load-pulled method, consistent with implementing a preferred embodiment of the present invention. With the load-pulled method, a cavity 901 is first loaded with the molecular sieves and the sample. A microwave oscillator 903 then propagates microwaves through the molecular sieves. A frequency counter 905 detects the frequency of the oscillator and measurement system with the molecular sieve. Additionally, the incident and reflected power could be a measured parameter. A microprocessor 907 then generates a moisture content reading 909 from the frequency readings from frequency counter 905.

FIG. 9B shows a microwave system equipped for measuring phase and amplitude of the incident and reflected waves, for example. Microwave oscillator 911 transmits microwaves to a power splitter 913. Power splitter 913 then outputs an incident power measurement 915 to microprocessor 917. Power splitter 913 also delivers a second output signal to directional coupler 919. Directional coupler 919 couples the signal from power splitter 913 with the signal from cavity 921, which is loaded with molecular sieves and sample, to generate a reflected power measurement 923 for microprocessor 917. The signal from cavity 921 is then used to generate a transmitted power measurement 925 for microprocessor 917. Microprocessor 917 then compares these measurements to a previously generated calibration to generate a moisture content reading 927 for the sample.

Since molecular sieves vary in methods of water absorption, size, and packing density, methods applicable to the particular type of sieve will be adapted to provide reproducible results. For example, the heat of absorption can be large and, therefore, a temperature measurement and correction may be needed. The packing density of the molecular sieve may require selection of a specific geometry of the molecular sieve (i.e. round, square, rectangle, etc.) to achieve reproducibility and ease of handling. Dense and viscous petroleum products may require special handling to successfully fill the sample container and to minimize air pockets. Also, the sample container may require a lid to prevent room moisture from entering.

In the present innovations, the reaction being used is preferably a non-equilibrium reaction. Therefore, in preferred embodiments it is irreversible and will run to completion if allowed. This is in contrast to an equilibrium reaction which is a reversible reaction and actually involves two reactions. There is a "forward" reaction and a mirror image "reverse" reaction. The reactants combine to form products. The products "decompose" to form reactants. Therefore, it is not necessary to determine whether the reaction has reached equilibrium or if certain factors, such as changes in the temperature or pressure, have unknowingly caused the equilibrium point to shift. Characterizing a non-equilibrium reaction eliminates these concerns.

However, the molecular sieves themselves would initially start with a mass transfer zone (MTZ) in the initial area where it first comes into contact with the sample. As time progresses, this mass transport zone continuously moves away from this initial area. Hence, upstream of the MTZ, the molecular sieves have reached equilibrium with the sample, while downstream of the MTZ, the molecular sieves are still in equilibrium with the air in the system.

A very important advantage of the disclosed innovations is that they provide a measurement technique which is suitable for field use.

Another important advantage of the disclosed innovations is that they provide a measurement technique which is suitable for use by relatively untrained personnel. With sample conditions and additives standardized as described herein, the sampling technician can be allowed to use the measurement unit simply as a black box.

Another important advantage is that the testing of the sample bottles is nondestructive. Thus some fraction of sample bottles can be systematically retained, if desired, for rechecking in case of later dispute.

Another important advantage is that the sample bottles, once filled with the fluid being tested, do not have to be reopened. Thus fluids, such as crude oil, which are environmentally undesirable can be properly disposed of simply by putting the filled bottles in appropriate disposal containers.

In one important class of embodiments, sample containers and sorbents as described above are used for field assay at the point where a tanker is being loaded or unloaded. This very simple assay-at-lading technique provides simple verification of crude oil assay, and hence reduced commercial disputes.

In another class of embodiments, standardized sample bottles as described above can be used for field sampling (e.g. at sample collection tap valves at dockside), and the electronic measurement can be done in a unit which is transportable, but not normally hand-carried. Thus for example a field auditor might fill a dozen labelled sample bottles at various points in a pumping facility, and then return to the analyzer in his truck, which is calibrated as described above, to obtain moisture analysis for each.

According to another disclosed class of innovative embodiments, there is provided: A method for determining moisture content of a fluid, comprising the steps of: placing a fluid in a package of molecular sieve; loading the fluid-filled package in a microwave measurement system; and measuring scattering parameters whereby the moisture content of said fluid is estimated.

According to a disclosed class of innovative embodiments, there is provided: A system for determining moisture content of a fluid, comprising: a package of molecular sieve; a microwave measurement system; wherein a fluid is placed in the package and loaded in the microwave measurement system for measurement of scattering parameters.

According to a disclosed class of innovative embodiments, there is provided: A method for field-testing moisture content in a fluid, comprising the steps of: mixing a pre-measured and separately packaged quantity of a selective absorbent material into a fluid to be tested; electrically characterizing said pre-measured quantity of said selective absorbent material and fluid, using an electrical measurement stage which is electromagnetically coupled thereto; and which outputs a test signal which is dependent on the permittivity of the selective absorbent material and fluid; and calculating and then outputting, from at least one stored calibration value for said electrical measurement stage and said pre-measured quantity of the selective absorbent material and the fluid, an indicated moisture content value.

According to a disclosed class of innovative embodiments, there is provided: A method for field-testing moisture content in a non-aqueous fluid, comprising: mixing a selective absorbent material into a fluid to be tested; electrically characterizing said pre-measured quantity of said selective absorbent material, using an electrical measurement stage which is electromagnetically coupled thereto and which outputs a test signal which is dependent on the permittivity of the sample; and calculating and then outputting, from at least one stored calibration value for said electrical measurement stage and said pre-measured quantity of said selective absorbent material and said fluid, an indicated moisture content value.

According to a disclosed class of innovative embodiments, there is provided: A method for field-testing moisture content in a non-aqueous fluid, comprising: a) mixing a pre-formulated selective absorbent material into a fluid to be tested; b) electrically characterizing said selective absorbent material after contact with said fluid, using an electrical measurement stage which is electromagnetically coupled thereto and which outputs a test signal which is dependent on the permittivity of the sample; c) draining said fluid from said absorbent material; and at two or more iterations of said steps a through c, calculating from at least one stored calibration value for said electrical measurement stage and said pre-measured quantity of said selective absorbent material and said fluid, a starting moisture loading value for said absorbent, a resulting moisture loading value for said absorbent, and calculating therefrom and then outputting an indicated moisture content value.

According to a disclosed class of innovative embodiments, there is provided: A field-testing system for analysis of moisture content in non-aqueous fluids, comprising: an electrical measurement stage which is electromagnetically coupled to a sample and which outputs a test signal which is dependent on the permittivity of the sample; and a pre-measured and separately packaged quantity of a selective absorbent material; wherein said electrical measurement stage is pre-calibrated for said pre-measured quantity of said selective absorbent material; and a calculation stage which looks up the output of said electrical measurement stage to obtain an indicated moisture content value.

According to a disclosed class of innovative embodiments, there is provided: A system for characterizing a sample, comprising: an oscillator measurement system; a sample container holding the sample and a molecular sieve material; wherein the sample is characterized by a change in a property of a signal of the oscillator measurement system; and wherein the oscillator measurement system is pre-calibrated for the container and molecular sieve material.

According to a disclosed class of innovative embodiments, there is provided: A method of testing a sample, comprising the steps of: using an apparatus that detects change in scattering parameters to characterize one or more known materials to obtain one or more baselines; testing an unknown material to detect scattering parameters to obtain a result; comparing the result with the one or more baselines wherein the apparatus is pre-calibrated for a container and a molecular sieve material.

Definitions

Following are short definitions of the usual meanings of some of the technical terms which are used in the present application. (However, those of ordinary skill will recognize whether the context requires a different meaning.) Additional definitions can be found in the standard technical dictionaries and journals.

The term "molecular sieve" includes both synthetic and naturally occurring zeolites, as well as any other material that can effectively be used to sequester, restrain or retain molecules in a material, such as (but not limited to) water molecules in a non-aqueous liquid, whether by physical capture within a crystalline structure, absorption, adsorption, hydrogen bonding, or other means including wherein the sieve behaves as a reactant in bonding with a material.

A list of zeolytes is provided for purposes of inclusion, and is not intended to limit the number of materials capable of being implemented in the present invention as a molecular sieve material:

| Code | Abbreviated Name | Full name |
|---|---|---|
| ABW | | Li-A (Barrer and White) |
| ACO | ACP-1 (one) | Aluminium Cobalt Phosphate-one |
| AEI | AlPO$_4$-18 (eighteen) | Aluminophosphate-eighteen |
| AEL | AlPO$_4$-11 (eleven) | Aluminophosphate-eleven |
| AEN | AlPO-EN3 | Aluminophosphate ethylenediamine (en)-3 |
| AET | AlPO$_4$-8 (eight) | Aluminophosphate-eight |
| AFI | AlPO$_4$-5 (five) | Aluminophosphate-five |
| AFO | AlPO$_4$-41 (forty-one) | Aluminophosphate-forty-one |
| AFR | SAPO-40 (forty) | Silico-Aluminophosphate-forty |
| AFS | MAPSO-46 (forty-six) | MgAl(P,Si)O$_4$-46 |
| AFT | AlPO$_4$-52 (fifty-two) | |
| AFX | SAPO-56 (fifty-six) | Silico-Aluminophosphate-fifty-six |
| AFY | CoAPO-50 (fifty) | |
| AHT | AlPO$_4$-H2 (two) | |
| APC | AlPO$_4$-C | |
| APD | AlPO$_4$-D | |
| AFN | AlPO$_4$-14 (fourteen) | |
| AST | AlPO$_4$-16 (sixteen) | |
| ATN | MAPO-39 (thirty-nine) | MgAlPO$_4$-thirty-nine |
| ATT | AlPO$_4$-12 (twelve)-TAMU | AlPO$_4$-12-Texas A & M University |
| ATV | AlPO$_4$-25 (twenty-five) | |
| AWO | AlPO$_4$-21 (twenty-one) | |
| AWW | AlPO$_4$-22 (twenty-two) | |
| BPH | | Beryllophosphate-Harvey (or hexagonal) |
| CGF | CoGaPO-5 (five) | Cobalt-Gallium-Phosphate-five |
| CGS | CoGaPO-6 (six) | Cobalt-Gallium-Phosphate-six |
| CON | CIT-1 (one) | California Institute of Technology-one |
| CFI | CIT-5 (five) | California Institute of Technology-five |
| CZP | | Chiral Zincophosphate |
| DDR | Deca-dodecasil 3R | Deca- & dodecahedra, 3 layers, rhombohedral |
| DFO | DAF-1 (one) | Davy Faraday Research Laboratory - one |
| DFT | DAF-2 (two) | Davy Faraday Research Laboratory - two |
| DOH | Dodecasil 1H | Dodecahedra, 1 layer, hexagonally stacked |
| DON | UTD-1 (one) | University of Texas at Dallas-one |
| EAB | | TMA-E (Aiello and Barrer) |
| EMT | EMC-2 (two) | Elf (or Ecole Supérieure) Mulhouse Chimie - two |
| ESV | ERS-7 (seven) | Eniricerche-molecular-sieve-seven |
| EUO | EU-1 (one) | Edinburgh University - one |
| IFR | ITQ-4 (four) | Instituto de Tecnologia Quimica Valencia - four |
| ISV | ITQ-7 (seven) | Instituto de Tecnologia Quimica Valencia - seven |

-continued

| Code | Abbreviated Name | Full name |
|---|---|---|
| ITE | ITQ-3 (three) | Instituto de Tecnologia Quimica Valencia - three |
| JBW | | NaJ (Barrer and White) |
| KFI | ZK-5 (five) | Zeolite Kerr - five |
| LOS | Losod | Low sodium aluminosilicate |
| LTA | Linde Type A | Zeolite A (Linde Division, Union Carbide) |
| LTL | Linde Type L | Zeolite L (Linde Division, Union Carbide) |
| LTN | Linde Type N | Zeolite N (Linde Division, Union Carbide) |
| MEI | ZSM-18 (eighteen) | Zeolite Socony Mobil - eighteen |
| MEL | ZSM-11 (eleven) | Zeolite Socony Mobil - eleven |
| MFI | ZSM-5 (five) | Zeolite Socony Mobil - five |
| MFS | ZSM-57 (fifty-seven) | Zeolite Socony Mobil - fifty-seven |
| MSO | MCM-61 (sixty-one) | Mobil Composition of Matter-sixty-one |
| MTN | ZSM-39 (thirty-nine) | Zeolite Socony Mobil - thirty-nine |
| MTT | ZSM-23 (twenty-three) | Zeolite Socony Mobil - twenty-three |
| MTW | ZSM-12 (twelve) | Zeolite Socony Mobil - twelve |
| NES | NU-87 (eighty-seven) | New (ICI) - eighty-seven |
| NON | Nonasil | Nonahedra, all silica composition |
| OSI | UiO-6 (six) | University of Oslo-six |
| RSN | RUB-17 (seventeen) | Ruhr University Bochum - seventeen |
| RTE | RUB-3 (three) | Ruhr University Bochum - three |
| RTH | RUB-13 (thirteen) | Ruhr University Bochum - thirteen |
| RUT | RUB-10 (ten) | Ruhr University Bochum - ten |
| SBE | UCSB-8 (eight) | University of California, Santa Barbara-eight |
| SBS | UCSB-6 (six) | University of California, Santa Barbara-six |
| SBT | UCSB-10 (ten) | University of California, Santa Barbara-ten |
| SAO | STA-1 (one) | University of Saint Andrews-one |
| SAT | STA-2 (two) | University of Saint Andrews-two |
| SGT | Sigma-2 (two) | |
| SFF | SSZ-44 (forty-four) | Standard Oil Synthetic Zeolite - forty-four |
| STF | SSZ-35 (thirty-five) | Standard Oil Synthetic Zeolite - thirty-five |
| STT | SSZ-23 (twenty-three) | Standard Oil Synthetic Zeolite - three) |
| TON | Theta-1 (one) | |
| TSC | Tschörtnerite | Jochen Tschörtner, finder of the mineral |
| VFI | VPI-5 (five) | Virginia Polytechnic Institute - five |
| VSV | VPI-7 (seven) | Virginia Polytechnic Institute - seven |
| ZON | ZAPO-M1 (one) | $(Zn,Al)PO_4$-Mulhouse - one |

Further, the size of molecular sieve material can vary, including the diameter of pellets if that is the form in which they are used. For example, in preferred embodiments of the present invention, smaller pellets are preferred to increase surface area available for molecular capture or transport. For example, a 1/16" diameter pellet is used in one preferred embodiment.

The term "microwave signals" is used to encompass all waves that travel from 1 Mhz up to and including infrared frequencies.

The term "electromagnetic characteristics" includes electrical and/or magnetic characteristics.

The terms "absorbent" and "adsorbent" are used throughout this specification, and are intended to broadly refer to the sequestration or capture of molecules or materials, and not necessarily to the limited ideas of surface or interior capture of molecules or materials. In general, the terms "absorbent" and "adsorbent" are intended to cover any of the ways that molecular sieve materials capture or contain or restrain or separate molecules from other types of molecules, such as water from oil.

An important advantage of the preferred embodiments is that the sorbent material fills a relatively high fraction of the volume of the container. This means that the electrical measurement stage will be strongly affected by changes in the electrical properties of the sorbent, as opposed to the crude oil (or other fluid) being measured. (The electrical characteristics of the fluid itself can be strongly affected by emulsion characteristics, including droplet size and structure and the continuous phase if any, as well as salinity or other contaminants.)

Another important advantage of the preferred embodiments is that it provides a field-usable electrical assay technique which is fairly insensitive to emulsion properties (e.g. droplet size).

MODIFICATIONS AND VARIATIONS

As will be recognized by those skilled in the art, the innovative concepts described in the present application can be modified and varied over a tremendous range of applications, and accordingly the scope of patented subject matter is not limited by any of the specific exemplary teachings given.

In one embodiment, the present invention comprises equipment suitable for use in field testing, such as an easily-assembled kit of limited weight. In one preferred embodiment, such a field test kit weighs less than three pounds, and includes a microwave oscillator circuit, preferably housed in aluminum, a container for holding molecular sieve and a sample, and other equipment for preferably siphoning the sample through the molecular sieve. FIG. 5, for example, shows one example setup consistent with such an embodiment.

In preferred embodiments, the present invention uses an oscillator system, such as an electrical oscillator system, and more specifically a microwave oscillator system. The exact frequency range of the oscillator can vary from implementation to implementation, and the examples given herein of a microwave oscillator are not intended to limit the invention to only those frequencies. Other frequencies that suitably interact with a sample in such a way that changes in the signal can be detected, such as by measuring scattering parameters. For example, in a load pulled system, the frequency of the oscillator is affected by the sample, which changes the frequency at which the oscillator oscillates. Alternately, transmitted, reflected, and/or incident waves can be affected by the probed material and detected. In such examples, the permittivity of the system seen by the oscillator changes when the sample is introduced, and this change is detected via measuring the scattering parameters, for example. Though we herein characterize the change in the tested system as a change in permittivity, other characterizations are also possible and within the scope of the present invention.

One advantage of the present invention includes a decrease in error for determining, for example, the water content of a crude oils sample. Human operators can damage equipment, ruin calibration or settings, and influence the apparatus in other ways when handling sensitive testing equipment in the field. In the present invention, pre-packaged molecular sieves and the general hardiness and simplicity of the testing process and apparatus reduce human actions that must be taken in order to obtain an estimate of water content in the sample. Further, a field test kit of the present innovations requires no trained technician for operation, and can be safely and effectively used by unskilled operators.

In one embodiment, the present invention allows testing of, for example, crude oil as it is in transport or exchanging possession, ownership, crossing political or legal boundaries, containers, etc. For example, crude oil unloaded from a ship to a new political boundary often requires an assessment of the actual amount of oil, which in turn requires an assessment of the amount of water in the offloaded liquid. The innovations of the present application provide an easy and effective means of providing the necessary information.

In yet another embodiment, the innovations herein described are used to test other materials. For example, the methanol in a solvent, or hexane in a solvent, or ketones in a solvent could be characterized using innovations of the present application.

In yet another embodiment, a "patch probe" is implemented, having only a surface area of molecular sieve material exposed to absorb liquids or molecules from a tested material.

Although the present application describes methods and systems for detecting the moisture content in crude oil, the present innovations may also be used with a solvent to detect used to detect the moisture content Due to the fact that molecular sieves can adsorb huge quantities of water, purging the sample and leaving the molecular sieves in the chamber could allow more analyses to be performed without changing the molecular sieves if the unit is properly calibrated. The same molecular sieves could then be used until they approach saturation.

The same package may be used for transporting and loading the sample in the microwave measurement system.

Different testing packages may be used depending on the pH of the sample and the solvent used (at least for special-applications, e.g. a Teflon or glass bottle for hot solvents).

The sample bottle may be resealed for convenient disposal of hazardous solvents. This would help in the transportation of the sample titer to the hazardous waste disposal through the laboratory ambient.

To minimize disposal and avoid contamination of the next sample, a sample port with a backpurge or flush-through maybe used to blow back the sample into the main tank.

It is also noted that the present innovations preferably occur in a non-equilibrium system, though the molecular sieve and tested material can of course be tested under equilibrium conditions in less preferred embodiments.

In a further alternative embodiment, the sample bottle can already be prefilled with the sorbent material. Thus the sample bottle itself hermetically protects the zeolite, or other sorbent, from moisture contamination before the sample is introduced.

In a further alternative embodiment, the beads of the zeolite, or other sorbent, can be fused or glued into a rigid mass with open pores. This permits more certainty that absorbent material will not be lost during transfer into the container. However, this embodiment makes it more difficult to fill the container, so this embodiment may be more advantageous with vacuum filling methods.

Note that, in some embodiments, it is not strictly necessary for the sorbent to fill the measuring container, as long as the volume of strong electric-field coupling to the electrical probe(s) is filled.

In a further class of alternative embodiments a precalibrated container and sorbent can be used for moisture assay of dry materials, such as flour or other stocks for food or feed or pharmaceutical preparation.

In some embodiments it is preferable to shake or stir the sample just before insertion into the measurement unit, to minimize the effect of separations which may occur in the liquid phase.

None of the description in the present application should be read as implying that any particular element, step, or is an essential element which must be included in the claim scope: THE SCOPE OF PATENTED SUBJECT MATTER IS DEFINED ONLY BY THE ALLOWED CLAIMS. Moreover, none of these claims are intended to invoke paragraph six of 35 USC section 112 unless the exact words "means for" are followed by a participle.

The claims as filed are intended to be as comprehensive as possible, and NO subject matter is intentionally relinquished, dedicated, or abandoned.

What is claimed is:

1. A method for determining moisture content of a fluid, comprising the steps of:
   opening a sealed package of molecular sieve;
   placing a sample of said fluid into said package of molecular sieve wherein said molecular sieve removes said moisture content from said sample;
   removably loading the fluid-filled package into a microwave measurement system to thereby occupy a volume in a microwave cavity thereof; and
   measuring scattering parameters to thereby estimate said moisture content of said fluid.

2. The method of claim 1, wherein the microwave measurement system uses load-pulled frequency measurement.

3. The method of claim 1, wherein the scattering parameters are selected from the group consisting of: reflections, transmission losses, amplitudes, and phase angles.

4. The method of claim 1, wherein the package is resealable.

5. The method of claim 1, wherein the molecular sieve is a zeolite.

6. The method of claim 1, wherein the package is disposable.

7. The method of claim 1, wherein the fluid is a multiphase fluid selected from the group: a non-aqueous fluid with a water phase, crude petroleum oil with a water phase, and refined petroleum products with a water phase.

8. A method for determining moisture content of a fluid, comprising the steps of:
   placing a sample of said fluid into a package of molecular sieve, wherein said package of molecular sieve is foil-sealed;
   loading the fluid-filled package into a microwave measurement system; and
   measuring scattering parameters to thereby estimate the moisture content of said fluid.

9. The method of claim 8, wherein the fluid is a multiphase fluid selected from the group: a non-aqueous fluid with a water phase, crude petroleum oil with a water phase, and refined petroleum products with a water phase.

10. A method for determining moisture content of a fluid, comprising the steps of:
    opening a sealed package of molecular sieve;
    placing a sample of the fluid and the molecular sieve into a container before being loaded in the microwave measurement system wherein said molecular sieve removes said moisture content from said sample;
    removably loading said container holding said sample and said molecular sieve into a microwave measurement system to thereby occupy a volume in a microwave cavity thereof;
    measuring scattering parameters to thereby estimate said moisture content of said fluid; and cleaning and reusing or disposing of the container after measuring scattering parameters.

11. The method of claim 10, wherein the container is selected from the group consisting of: a paper container and a plastic container.

12. The method of claim 10, wherein the container is made of a material not significantly absorptive of microwave energy.

13. The method of claim 10, wherein the fluid is a multiphase fluid selected from the group: a non-aqueous fluid with a water phase, crude petroleum oil with a water phase, and refined petroleum products with a water phase.

14. A system for determining moisture content of a fluid, comprising:
a package of molecular sieve having a sample of the fluid placed therein wherein said molecular sieve removes said moisture content from said sample; and
a microwave measurement system into which said package has been removably loaded to thereby occupy a volume of a microwave cavity thereof;
wherein said microwave measurement system is adapted to be electromagnetically coupled to said package containing said fluid for measurement of scattering parameters to thereby estimate said moisture content of said fluid.

15. The system of claim 14, wherein the fluid and the molecular sieve are placed into a plastic or paper container before being loaded in the microwave measurement system.

16. The system of claim 14, wherein the fluid and package are placed in a container made of a material that does not significantly absorb microwave energy before being loaded in the microwave measurement system.

17. The system of claim 14, wherein the microwave measurement system uses load-pulled frequency measurements.

18. The system of claim 14, wherein the scattering parameters are selected from the group consisting of: reflections, transmission losses, amplitudes, and phase angles.

19. The system of claim 14, wherein the package is resealable.

20. The system of claim 14, wherein the molecular sieve is a zeolite.

21. The system of claim 14, wherein the package is disposable.

22. The method of claim 14, wherein the fluid is a multiphase fluid selected from the group: a non-aqueous fluid with a water phase, crude petroleum oil with a water phase, and refined petroleum products with a water phase.

23. The method of claim 15, wherein the fluid is a multiphase fluid selected from the group: a non-aqueous fluid with a water phase, crude petroleum oil with a water phase, and refined petroleum products with a water phase.

24. A system for determining moisture content of a fluid, comprising:
a foil-sealed package of molecular sieve;
a microwave measurement system;
wherein a sample of said fluid is placed in the package; and
wherein said package loaded into the microwave measurement system for measurement of scattering parameters to thereby estimate the moisture content of said fluid.

25. The method of claim 24, wherein the fluid is a multiphase fluid selected from the group: a non-aqueous fluid with a water phase, crude petroleum oil with a water phase, and refined petroleum products with a water phase.

26. A method for determining moisture content of a fluid, comprising the steps of:
opening a sealed package of molecular sieve;
combining a sample of said fluid with a package of molecular sieve wherein said molecular sieve removes said moisture content from said sample;
removably loading the fluid-filled molecular sieve material into a microwave measurement system, thereby occupying a volume of a microwave cavity thereof; and
measuring scattering parameters, to thereby estimate said moisture content of said fluid.

27. The method of claim 26, wherein said package of molecular sieve is foil sealed.

28. The method of claim 26, further comprising the steps of:
placing said sample of the fluid and said molecular sieve combined therein into a container before being removably loaded in the microwave measurement system; and
disposing of the container after measuring scattering parameters.

29. The method of claim 28, wherein the container is selected from the group consisting of: a paper container and a plastic container.

30. The method of claim 28, wherein the container is made of a material not significantly absorptive of microwave energy.

31. The method of claim 28, wherein the fluid is a multiphase fluid selected from the group: a non-aqueous fluid with a water phase, crude petroleum oil with a water phase, and refined petroleum products with a water phase.

32. The method of claim 26, wherein the microwave measurement system uses load-pulled frequency measurement.

33. The method of claim 26, wherein the scattering parameters are selected from the group consisting of: reflections, transmission losses, amplitudes, and phase angles.

34. The method of claim 26, wherein the package is resealable.

35. The method of claim 26, wherein the molecular sieve is a zeolite.

36. The method of claim 26, wherein the package is disposable.

37. The method of claim 26, wherein the fluid is a multiphase fluid selected from the group: a non-aqueous fluid with a water phase, crude petroleum oil with a water phase, and refined petroleum products with a water phase.

38. A system for determining moisture content of a fluid, comprising:
a sample of said fluid having been combined with a package of molecular sieve wherein said molecular sieve removes said moisture content from said sample; and
a microwave measurement system into which said molecular sieve material has been removably loaded to thereby occupy a volume of a microwave cavity thereof;
wherein said microwave measurement system is adapted to be electromagnetically coupled to said sample for measurement of scattering parameters.

39. The method of claim 38, wherein said package of molecular sieve is foil sealed.

40. The system of claim 38, wherein said sample of the fluid and said molecular sieve combined therein are placed into a plastic or paper container before being removably loaded in the microwave measurement system.

41. The method of claim 40, wherein the fluid is a multiphase fluid selected from the group: a non-aqueous fluid with a water phase, crude petroleum oil with a water phase, and refined petroleum products with a water phase.

42. The system of claim 38, wherein said sample of the fluid and said molecular sieve contained therein are placed in a container made of a material that does not significantly absorb microwave energy before being removably loaded in the microwave measurement system.

43. The system of claim 38, wherein the microwave measurement system uses load-pulled frequency measurements.

44. The system of claim 38, wherein the scattering parameters are selected from the group consisting of: reflections, transmission losses, amplitudes, and phase angles.

45. The system of claim 38, wherein the package is resealable.

46. The system of claim 38, wherein the molecular sieve is a zeolite.

47. The system of claim 38, wherein the package is disposable.

48. The method of claim 38, wherein the fluid is a multiphase fluid selected from the group: a non-aqueous fluid with a water phase, crude petroleum oil with a water phase, and refined petroleum products with a water phase.

* * * * *